United States Patent [19]

Hisamichi et al.

[11] Patent Number: 4,945,366

[45] Date of Patent: Jul. 31, 1990

[54] ENDOSCOPE STILL PHOTOGRAPHING APPARATUS PROVIDED WITH AN AUTOMATIC ILLUMINATING LIGHT AMOUNT CONTROLLING FUNCTION

[75] Inventors: Yasushi Hisamichi, Hachioji; Akihiko Miyazaki, Nagoya, both of Japan

[73] Assignee: Olympus Optical Co. Ltd., Tokyo, Japan

[21] Appl. No.: 335,417

[22] Filed: Apr. 10, 1989

[30] Foreign Application Priority Data

Sep. 21, 1988 [JP] Japan .................... 63-237184

[51] Int. Cl.⁵ .............................. G03B 29/00
[52] U.S. Cl. .................................. 354/62
[58] Field of Search ........................... 354/62

[56] References Cited

U.S. PATENT DOCUMENTS 4,353,630  10/1982  Ito et al. ................. 354/29

FOREIGN PATENT DOCUMENTS 61-13236  1/1986  Japan .

Primary Examiner—Michael L. Gellner
Attorney, Agent, or Firm—Armstrong, Nikaido, Marmelstein, Kubovcik & Murray

[57] ABSTRACT

In a releasing operation with a still camera fittable to the eyepiece part of an endoscope and containing a recording medium, without exposing the recording medium, the diaphragmed value of a light source apparatus is set at a value adapted to the photographing condition and then the recording medium is actually exposed.

7 Claims, 5 Drawing Sheets

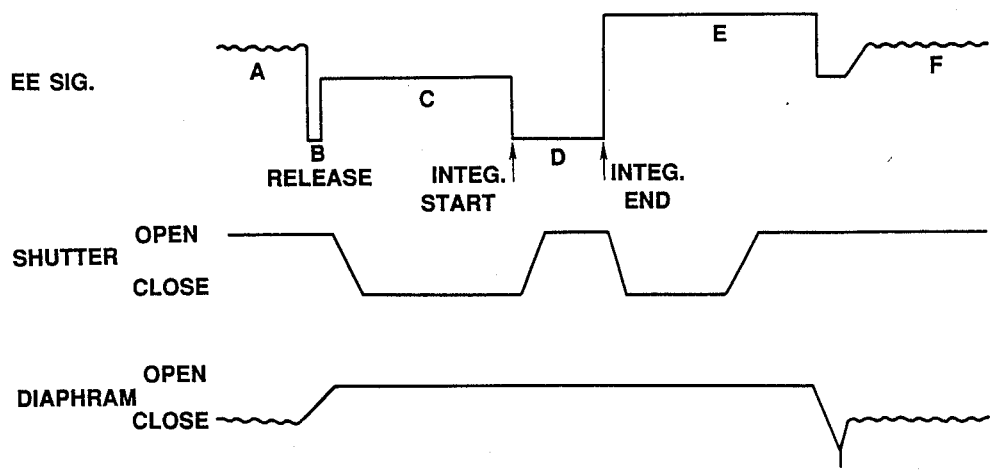
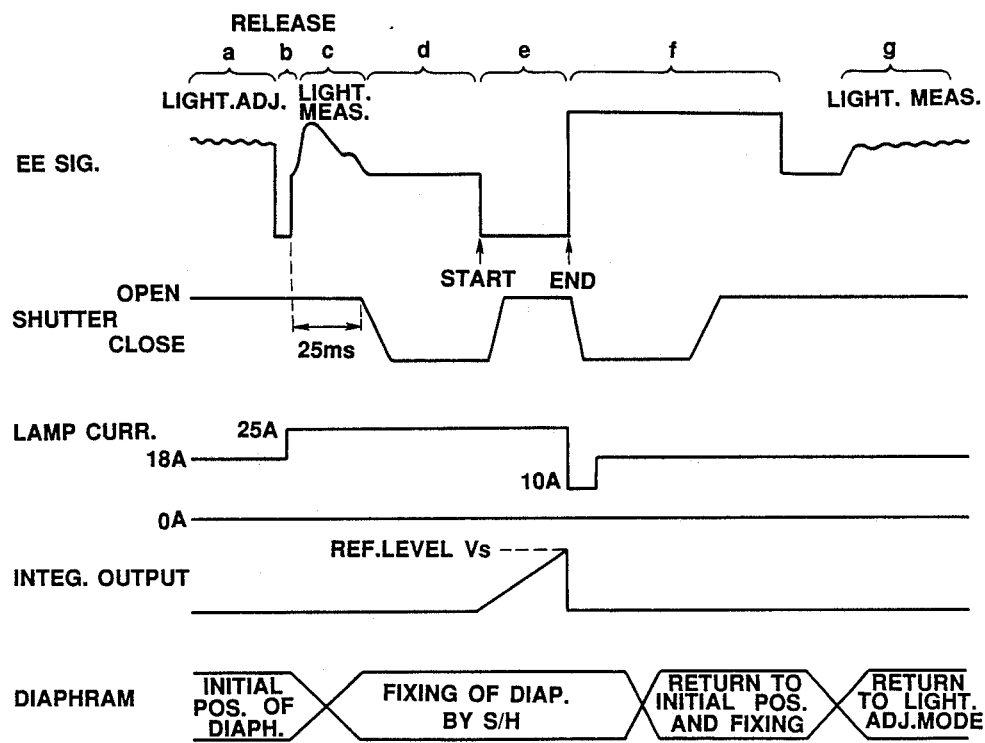

ENDOSCOPE STILL PHOTOGRAPHING APPARATUS PROVIDED WITH AN AUTOMATIC ILLUMINATING LIGHT AMOUNT CONTROLLING FUNCTION

BACKGROUND OF THE INVENTION

1. Field of the Invention and Related Art Statement:

This invention relates to an endoscope still photographing apparatus provided with a control means setting the illuminating light amount to be of the optimum value before starting an exposure.

Recently, an endoscope has come to be extensively used in the medical field and industrial field.

Now, in order to make a detailed diagnosis with an endoscope or to know the variation with the lapse of time of an affected part, a photographing is often made. As disclosed, for example, in the publication of a Japanese Patent Application Laid Open No. 13236/1986, the assignee has suggested an apparatus wherein, in the case of photographing at a short distance, in order to make a controllable shutter speed, how much the diaphragm is to be diaphragmed at the time of photographing from the present EE level and diaphragm position is calculated and, in case the object at the short distance is very bright, the calculated diaphragm is diaphragmed to photograph the object so that the shutter speed may be within a controllable range to prevent an over exposure.

This photographing sequence shall be explained. The camera is to be fitted to the eyepiece part of the scope. If the diaphragm and shutter are incorporated on the camera side, the size will become so large as to reduce the operatability. Therefore, the diaphragm and shutter are incorporated on the light source side and are controlled with respective signals transmitted to the light source side from the camera side. In order to omit one of the signal lines, the diaphragm controlling signal and shutter controlling signal are transmitted through one line. FIG. 1 shows respective timing charts of the control signal (EE signal), shutter and diaphragm.

A: At the time of the automatic light adjustment, the diaphragm will be controlled by the signal (EE signal) obtained by converting the light from the image guide to an electric signal. The shutter remains open.

B: When a release signal is made within the camera, the shutter will tend to close and the diaphragm will tend to open.

C: The diaphragm opens and the shutter closes.

D: The shutter opens with an integration starting signal and closes with an integration ending signal. The diaphragm remains open.

E: When the mirror on the camera side closes and no light comes into the film, the shutter will open.

F: The state of A returns.

In the case of exposing at a short distance, the diaphragm will be diaphragmed for the period of D so as not to make an over exposure.

Such photographing sequence as in the above has been so far used.

However, in fact, if the light amount at that time is judged from the position of the diaphragm, it will be found that, in case the precision becomes low particularly in the diaphragmed direction and thereby the diaphragm is diaphragmed too much, the exposure amount will be well kept at the regulated value but the shutter speed will become so long that the exposure amount will be likely to collapse. In order to improve it, as explained in a Japanese Patent Application No. 195901/1982, the assignee has provided a hard means of controlling the diaphragm in the opening direction after the lapse of a fixed period after the starting of the exposure. Anyhow, with these methods, it is difficult to make the optimum diaphragmed amount and a large burden has been applied to the CPU forming the control means.

By the way, an exposure controlling means is disclosed in U.S. Pat. No. 4,353,630. However, even if this prior art example is applied to the endoscope still phototographing apparatus, the above mentioned problems will not able to be solved.

OBJECTS AND SUMMARY OF THE INVENTION

An object of the present invention is to provide an endoscope still photographing apparatus which can be positively set to an illuminating light amount adapted to still photographing.

Another object of the present invention is to provide an endoscope still photographing apparatus which can be realized at a low cost without requiring a high precesion diaphragm or the like.

In the present invention, in case the releasing operation is made, the recording medium is held not to be exposed, the diaphragm is moved and set to conform to the photographing condition and, after this setting, the recording medium is exposed so that no excess diaphragming may be caused and the illuminating intensity adapted to photographing may be always set to make a still photographing.

BRIEF DESCRIPTION OF THE DRAWINGS

FIG. 1 shows timing charts showing the operation of a prior art example.

FIGS. 2 to 5 relate to the first embodiment of the present invention.

FIG. 2 is a formation view of an endoscope still photographing ,apparatus of the first embodiment.

FIG. 3 is a formation view of a control apparatus in the first embodiment.

FIG. 4 shows timing charts showing the operation of the first embodiment of the present invention.

FIG. 5 is a flow chart showing the operation of the first embodiment.

DETAILED DESCRIPTION OF THE PREFERRED EMBODIMENT

Figure 2:
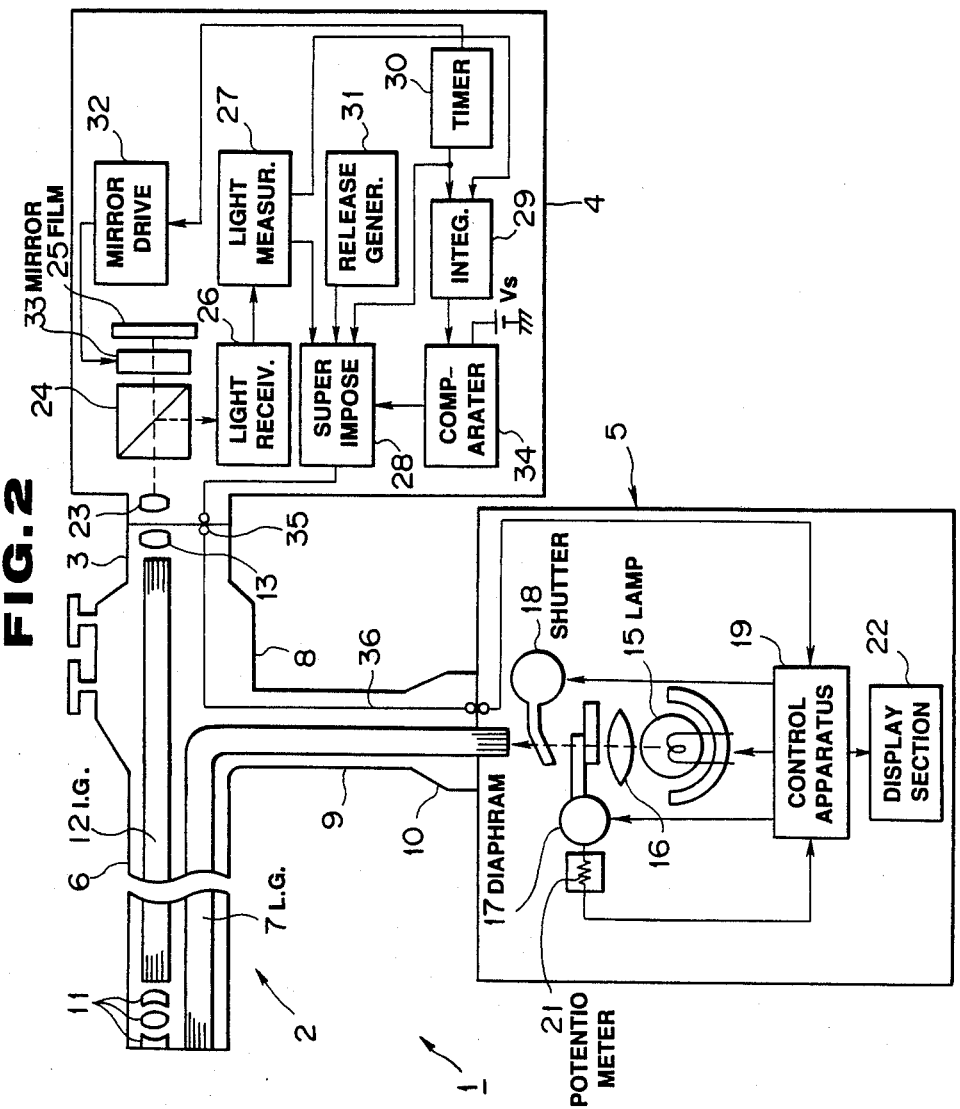

As shown in FIG. 2, an endoscope still photographing apparatus of the first embodiment comprises an endoscope 2, an endoscope photographic camera 4 fitted to an eyepiece part 3 of this endoscope 2 and a light source apparatus 5 feeding an illuminating light to the endoscope 2.

The above mentioned endoscope 2 has an elongate insertable part 6 which can be inserted into a body cavity or the like. A light guide 7 transmitting an illuminating light is inserted through this insertable part 6. A connector 10 of a light guide cable 9 extended out of an operating part 8 is fitted to the light source apparatus 5 so that the illuminating light may be fed to the entrance end surface of this light guide 7 formed of a flexible fiber bundle. When the illuminating light is fed to the entrance end surface of this light guide 7, the illuminating light will be transmitted through the light guide 7 and will be emitted from the exit end surface facing the tip surface of the insertable part 6 to illuminate an object. The image of the illuminated object is formed on the entrance end surface of an image guide 12 arranged in the focal plane of an objective lens system 11 by the objective lens system 11. This image guide 12 is formed of a flexible fiber bundle and transmits the optical image to the exit end surface on the eyepiece part 3 side. A magnified observation can be made with a naked eye through an eyepiece lens 13. When the camera 4 is fitted to this eyepiece part 3, a photographing will be able to be made.

The above mentioned light source apparatus 5 can condense the illuminating light emitted from a lamp 15 with a condenser lens 16 and can radiate it onto the entrance end surface of the light guide 7. In this case, a diaphragm 17 is interposed in the course of the illuminating light path to be able to control the transmitted light amount. Also, in the course of this illuminating light path, a shuuter 18 is further interposed so as to be controlled to open and close by a control apparatus 19.

The above mentioned controlling apparatus 19 can control the diaphragmed amount of the diaphragm 17. For example, a potentiometer 21 is fitted to this diaphragm 17 so as to be able to detect the diaphragmed amount. The control apparatus 19 can detect the diaphragmed amount state of the diaphragm 17 with the voltage value or the like of the variable resistance end in case a constant current is made to flow through this potentiometer 21. By the way, this diaphragmed amount can be displayed in a displaying section 22.

On the other hand, in the above mentioned camera 4, an image forming lens 23 is arranged as opposed to the eyepiece lens 13 so that, by this image forming lens 23, the optical image transmitted through the image guide 12 may be formed (exposed) on a film 25 arranged on the transmitted light side through a beam splitter 24. The light reflected by this beam splitter 24 is led to a light receiving device 26 which outputs an electric signal of a level corresponding to the received light amount. This electric signal is input into a light measuring circuit 27 which outputs a light measuring signal. At the time of an observation, this light measuring signal will be input as an EE signal into the control apparatus 19, within the light source apparatus 5 through a superimposing circuit 28 and will be input into an integrating circuit 29.

The above mentioned integrating circuit 29 starts an integrating operation with a timer signal output by a timer circuit 30 after a fixed time. This timer circuit 30 starts a time measuring operation (timer operation) with a release indicating signal from a release generator 31 provided in the camera 4 and outputs a timer signal after a fixed time (for example, 25 minutes) and this timer signal is input respectively into the integrating circuit 29, superimposing circuit 28 and mirror driving circuit 32.

The above mentioned release (indicating) signal is transmitted to the control apparatus 19 through the superimposing circuit 28 and the light measuring signal of the light measuring circuit 27 is EE-controlled as an EE signal so that an illuminating intensity adapted to photographing with the film 25 may be made by this release signal.

The above mentioned timer signal outputs a timer signal after the time required to be able to complete the operation of this EE control.

The mirror driving circuit 32 into which the timer signal is input rotates and retreats the mirror 33 leading the light transmitted through the beam splitter 24 to the finder (observing) side and leads the same light to the film 25 side, that is, to expose the film.

When the above mentioned film 25 is exposed, the integrating circuit 29 also will operate to integrate the light measuring signal of the light measuring circuit 27 and the output of this integrating circuit 29 will be input into a comparator 34.

A reference voltage $V_S$ is applied to the other input end of the above mentioned comparator 34. When the output signal of the integrating circuit reaches the level of this reference voltage $V_S$, the output level of the comparator 34 will be inverted (for example, from the "L" to "H" level), the exposure will end and an exposure end signal will be output. This end signal is input into the superimposing circuit 28.

This end signal is transmitted to the control apparatus 19 through the superimposing circuit 28 and the shutter 18 is closed. Also, the mirror 33 is switched to lead to the finder side the light transmitted through the beam splitter 24.

The above mentioned superimposing circuit 28 is connected with a contact contacted with an electric contact 35 provided on the eyepiece part 3 side in case the camera 4 is fitted to the eyepiece part 3, can transmit the light measuring signal, release signal, integration starting signal and light measurement end signal to the light source apparatus 5 through a cable 36 within the endoscope 2 and transmits the signals to the control apparatus 19 within the light source 5. On the basis of these transmitted signals, the control apparatus 19 makes such predetermined control as controlling the diaphragmed amount.

Figure 3:
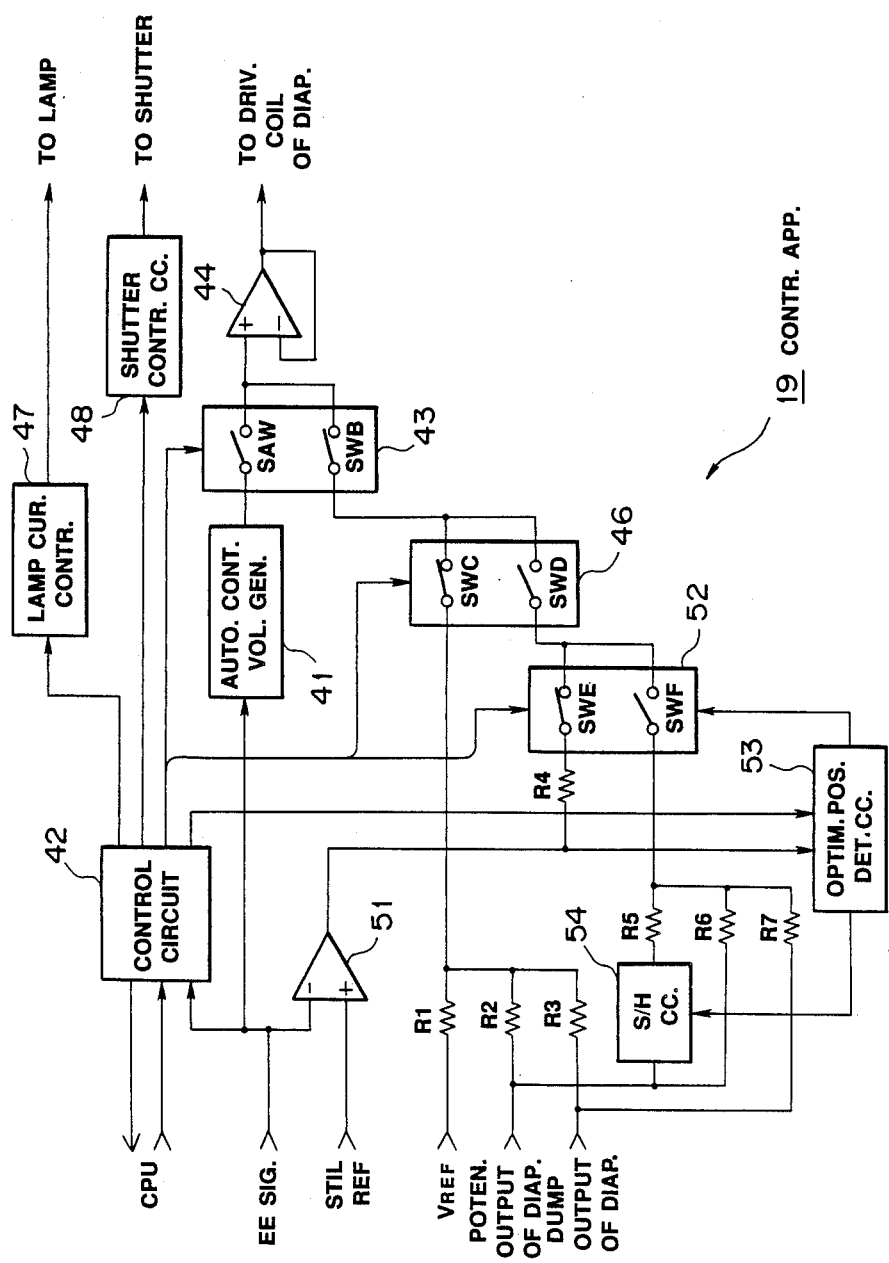

The formation of the above mentioned control apparatus 19 is shown in FIG. 3.

At the time of an observation, in case the light amount is automatically adjusted, the light measuring signal through the superimposing circuit 28 from the light measuring circuit 27 will be an EE signal and will be input into an AUTO control voltage generating circuit 41 and a control voltage will be produced.

This control voltage is input into a buffer circuit 44 through an operatively connecting switch 43 controlled to be on/off by a control circuit 42, controls the current value flowing through the driving coil of the diaphragm 17 to move the diaphragm 17 and controls the diaphragmed amount so that the EE level may be always constant. In such case, the above mentioned switch 43 will be controlled to be on/off by the control circuit 42 so that one switch SWA may close and the other switch SWB may open.

The above mentioned control circuit 42 controls the above mentioned switch 43 and others to be on/off by a controlling CPU.

In case the light amount is manually adjusted, a voltage $V_{REF}$ determining the diaphragmed amount, a potentio output from the potentiometer 21 representing the present diaphragmed amount and a damper output controlling the response of a diaphragm servo loop (by a damper coil wound concentrically with the driving coil moving the diaphragm 17, a current corresponding to the variation of the current flowing through the driving coil flows) are added respectively through resistances R1, R2 and R3 and are input into a switch SWB through one switch SWC of an operatively connecting switch 46 and a current is fed to the driving coil through this switch SWB. In such case, by the control circuit 42, the switches are controlled to be on/off so that one switch SWC may close and the other switch SWD may open and that, in the above mentioned switch 43, one switch SWA may open and the other switch SWB may close and, by holding the current flowed through the driving coil of the diaphragm 17 at the manually set constant current, the diaphramed amount can be fixed.

When a release signal is input as an EE signal into the control circuit 42 of the control apparatus 19 through the superimposing circuit 28 from the release generator 31 in such case that the release button of the endoscope photographic camera 4 is pressed, this control circuit 42 will elevate the lamp current output to the lamp 15 from a lamp current controlling circuit 47 and will increase the light amount of the lamp 15.

Also, the above mentioned control circuit 42 controls a shutter controlling circuit 48 to control the shutter to open and close so that, for example, when a release signal is input, the diaphragm will be set in the optimumr diaphragmed amount position and then the shutter 18 will be once closed and then will be opened in this optimum diaphragmed amount state to photograph.

Now, this embodiment has a great feature in the formation of a means whereby, in the case of an automatic photographing mode, just before actually photographing with a release operation, the diaphragmed amount will be moved and set in the optimum diaphragmed amount positiion in which an actual photographing will, be made.

The EE signal is applied to one input end of a comparator 51 and is compared with a voltage of STIL REF applied to the other input end and this compared output is applied to one switch SWE of an operatively connecting switch 52 through a resistance R4.

In this operatively connecting switch 52, in the case of the automatic photographing mode, when the above mentioned release signal is input the control circuit 42 will switch on one switch SWE which has been off and will feed the compared output to the driving coil of the diaphragm 17 through the switches SWD and SWB. That is to say, by varying the diaphragmed amount of the diaphragm 17 with this compared output, the diaphragmed position is set so that the level of the EE signal may coincide with the voltage of the STIL REF.

The above mentioned STIL REF represents a voltage of the EE signal when the optimum exposure intensity in the case of photographing is made. Therefore, in case the level of the EE signal is lower than of the STIL REF, the compared output of the comparator 51 will become, for example, "H". In this case, the diaphragm 17 will be operated in the direction of opening. On the other hand, when the level of the EE signal is higher than of the STIL REF, the diaphragm 17 will be moved in the direction of closing.

The output of the above mentioned comparator 51 is input into an optimum position detecting circuit 53 which takes in the above mentioned compared output, detects the position in which the level of the EE signal becomes equal to that of the STIL REF, outputs a sample holding pulse to a sample holding (S/H) circuit 54 at that time and holds as a sample the potentio output then of the diaphragm 17 until the photographing ends.

In the above mentioned optimum position detecting circuit 53, after the above mentioned sample holding pulse is output, one switch SWE is made off and connecting switch 52 and the output made by adding the potentio output sample-held in the sample holding circuit and output through the resistance R5, the potentio output through the resistance R6 and the damper output of the diaphragm 17 output through the resistance R7 is output to the switch SWF side and is further output to the driving coil of the diaphragm 17 through the switch SWD and the like. Thereby, the position of the diaphragm 17 is fixed until the photographing ends. BY the way, even if the diaphragm 17 is fully opened, in case the level of the EE signal does not reach the voltage of the STIL REF, the diaphragm 17 will be fixed as fully opened and the photographing time will only become longer.

When the above mentioned release signal is input into the control apparatus 19, the time until the diaphragm 17 is completely moved and set in the position of the STIL REF will be, for example, within 25 [m sec] and, therefore, the control circuit 42 will transmit this input release signal to the CPU which will output a signal of closing the shutter 18 to the control circuit 42 after 25 [m sec]. Thereby, the control circuit 42 will once close the shutter 18 through the shutter controlling circuit 48. By the way, the mirror 33 within the camera will not be immediately rotated (not be exposed) by the releasing operation but will be opened after the shutter 18 is closed.

Then, in the state of the optimum diaphragmed amount position sample-held in the above mentioned sample holding circuit 54, the photographing may be made.

The operation in the case of photographing in the automatic photographing state in this first embodiment shall be explained in the following.

The period before the leasing operation is represented by a in FIG. 4. In this period a, the diaphragm 17 is controlled by the EE signal so that the EE signal may be of a constant level adapted to the observation. In this case, the lamp 15 will emit a light when the lamp current is, for example, 18 [A] and the shutter 18 will be open.

When the release button of the endoscope photograph camera 4 is operated, the release generator 31 will generate a release signal which will be input into the superimposing circuit 28 and will output a trigger signal to the timer circuit 30. Also, as shown by b in FIG. 4, this release signal is input as an EE signal into the control apparatus 19.

When this release signal is input into the control apparatus 19, the lamp current will be elevated, for example, to 25 [A] through the control circuit 42 and lamp current controlling circuit 47 to increase the light amount. This release signal is transmitted to the CPU through the control circuit 42, opens the switches SWA, SWC and SWF, closes the swithches SWE and SWE and starts the light measuring operation for setting the diaphragmed value. This is shown by the reference symbol c in FIG. 4.

The EE signal as a light measuring signal and the STIL REF representing the voltage of the EE signal when the optimum exposure is made are compared with each other by the comparator 51 and the diaphragm 17 is moved so that the EE signal may be of the same voltage level as of the STIL REF. The output of this comparator 51 outputs a pulse sample-holding the sample holding circuit 54 at the timing when the diaphragm becomes to be of the same voltage as of the STIL REF and holds the potentio output then until photographing ends. Then, the switch SWE will open and the SWF will close. Thereby, the position of the diaphragm 17 will be fixed until the photographing ends. After the release signal is input, until the diaphragm 17 is in the position of the STIL REF, the diaphragmed amount will be within 25 [m sec]. When the release signal is received by the CPU from the control circuit 42, it will be output to the shutter controlling circuit 48 side through this control circuit 42 not immediately but after the delay of 25 [m sec] until the diaphragmed value setting ends. Thereby, as shown by the reference symbol d in FIG. 4, the shutter 18 will be closed and the feed of the light to the light guide will be stopped. Thereafter, the mirror 33 will rotate and retreat to set an exposable state.

On the other hand, the timer circuit 30 within the above mentioned endoscope photographic camera will be triggered by the release signal and, after the lapse of a fixed time, will output an integration starting signal to the superimposing circuit 28 and integrating circuit 29. As shown in FIG. 2, the EE signal as this integration starting signal is input into the control apparatus 19 within the light source apparatus 5. Therefore, the closed shutter 18 opens and starts exposure and the above mentioned integrating circuit 29 into which the output signal of the light measuring circuit 27 at the time of this exposure is input starts an integrating operation. When the integrated output of this integrating circuit 29 reaches a reference level Vs corresponding to the optimum exposure amount, the comparator 34 will output a light measurement end signal to the superimposing circuit 28. When the EE signal as this light measurement end signal is input into the control apparatus 19, the CPU will close the shutter 18 by the shutter controlling circuit 48 through the control circuit 42. This is shown by the reference symbol f in FIG. 4. Also, the lamp current is reduced by the lamp current controlling circuit 47 to a value (for example, 10 [A]) lower than at the time of the ordinary observation. In fact, it takes time since the light measurement end signal is output until the shutter 18 is perfectly closed. This time may cause over exposure. Therefore, the lamp current is reduced to prevent the over exposure. After the shutter 18 is closed, the diaphragm 17 is returned to the diaphragmed state before starting the photographing. (That is to say, the switch SWD is opened, the switch SWC is closed and the $V_{REF}$ is made the potentio output voltage before starting the photographing to make the state before starting the photographing.)

After a fixed period, the mirror 33 is returned to the observing side, the shutter 18 is opened and the opening and closing of each switch are returned to the state before starting the photographing. Thereby, the first photographing ends.

Figure 5:
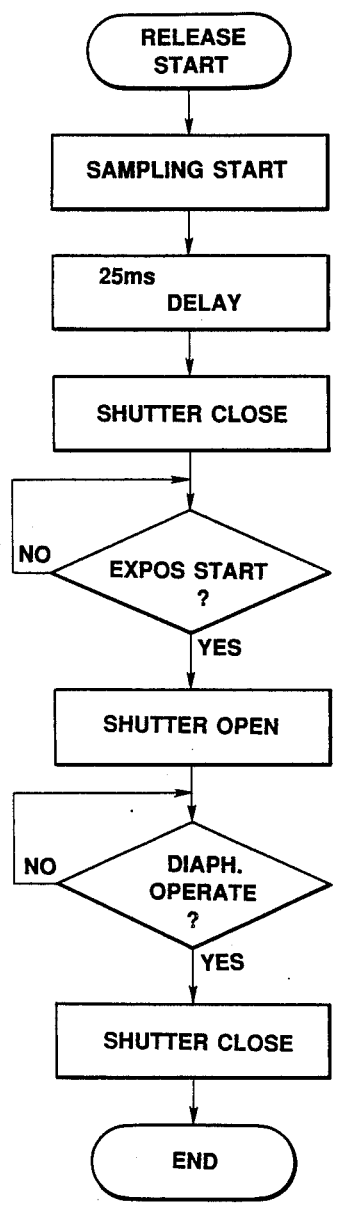

FIG. 5 shows a flow chart of the above mentioned first photographing operation.

According to this embodiment, within a short period just before the exposure is actually made, the photographing condition is set without exposing the film 25 and the optimum diaphragmed value position is detected and, after the diaphragmed value position is held, the exposure is actually made. Therefore, even in case the diaphragmed value is large, the optimum diaphragmed value will be able to be set and, under this optimum diaphragmed value condition, the photographing will be able to be made.

Therefore, the photographing can be made always under the optimum illuminating light intensity without such failure as over diaphragming.

Also, the CPU makes only the time delay of the release signal and such simple control as controlling the respective parts and is not subjected to a large burden and a photographing high in the exposure precision can be made.

As in this embodiment, after the releasing operation, without exposing the recording medium, the diaphragmed amount is set so as to coincide with the exposure intensity adapted to this recording medium and the set value is held to actually expose the recording medium. Therefore, there is no need of a high precision linearity and a wide dynamic range light measuring system or diaphragm controlling system.

That is to say, in the prior art example, by the releasing operation, a diaphragm controlling signal as to how much the diaphragm is diaphragmed from the level of the light measuring signal just before this releasing is produced and therefore, if the light measuring level at the time of the observation is different (depending on the sensitivity or the like of the recording medium) from the optimum level in the case of photographing, unless the difference of this light measuring level is small, the diaphragming at the time of photographing will be different from the optimum level.

Also, even if the difference of the light measuring level is small, if the linearity of the diaphragm or diaphragm driving means is low, the diaphragmed amount set by the light measuring level will be different from the optimum level and a wide dynamic range will be required.

Therefore, in the prior art example, the respective components low in the difference and high in the price must be used.

On the other hand, in this embodiment, the light measuring system and diaphragmimg system (illuminating system) are set in the actual exposing condition (not exposing the recording medium) to judge whether the condition coincides with the reference level or not and are held on the coinciding level and then the actual photographing is made. Therefore, even the light measuring system and diaphragm controlling system low in the linearity can be well used and can be made low in the cost.

Figure 6:
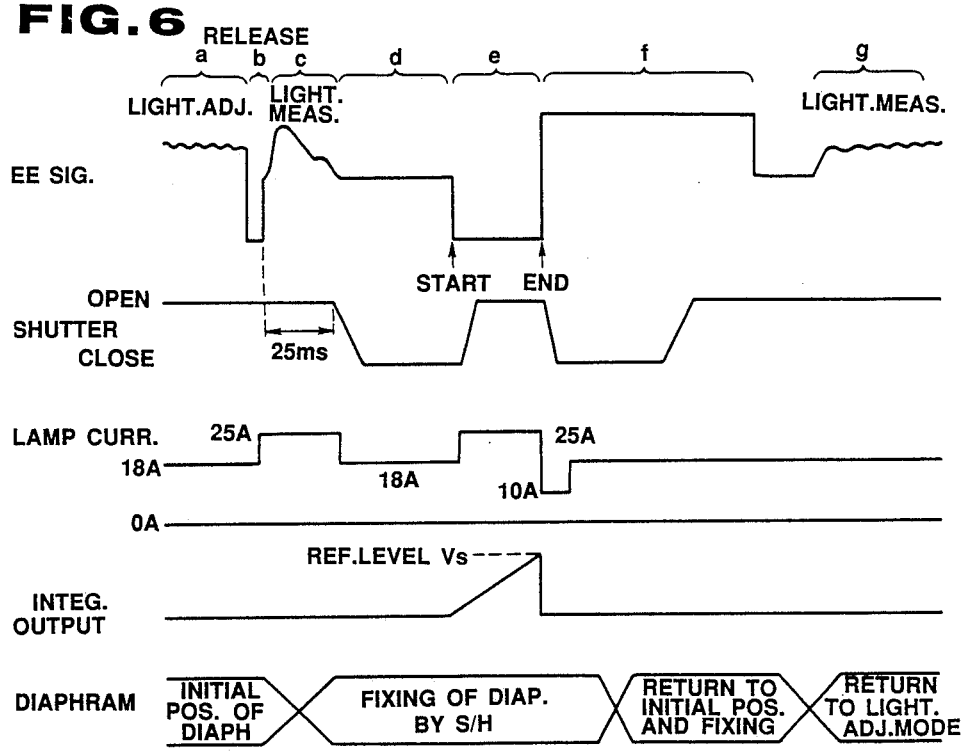
FIG. 6 shows timing charts showing the operation of the second embodiment of the present invention.

FIG. 6 shows timing charts in the second emboddiment of the present invention.

In this embodiment, after the release signal is output, for example, after 25 [ms], the lamp current is again lowered to 18 [A]and then, at the time of starting the integration, is again raised to 25 [A](the lamp is constantly lighted during the period of d).

Thus, there are advantages that the lamp can be made lower in the power consumption and longer in the life than in the first embodiment.

Also, there are advantages that the generated heat amount can be made smaller, the heat radiating means can be made smaller and the lighting apparatus can be made smaller. The others are the same as in the first embodiment.

Figure 7:
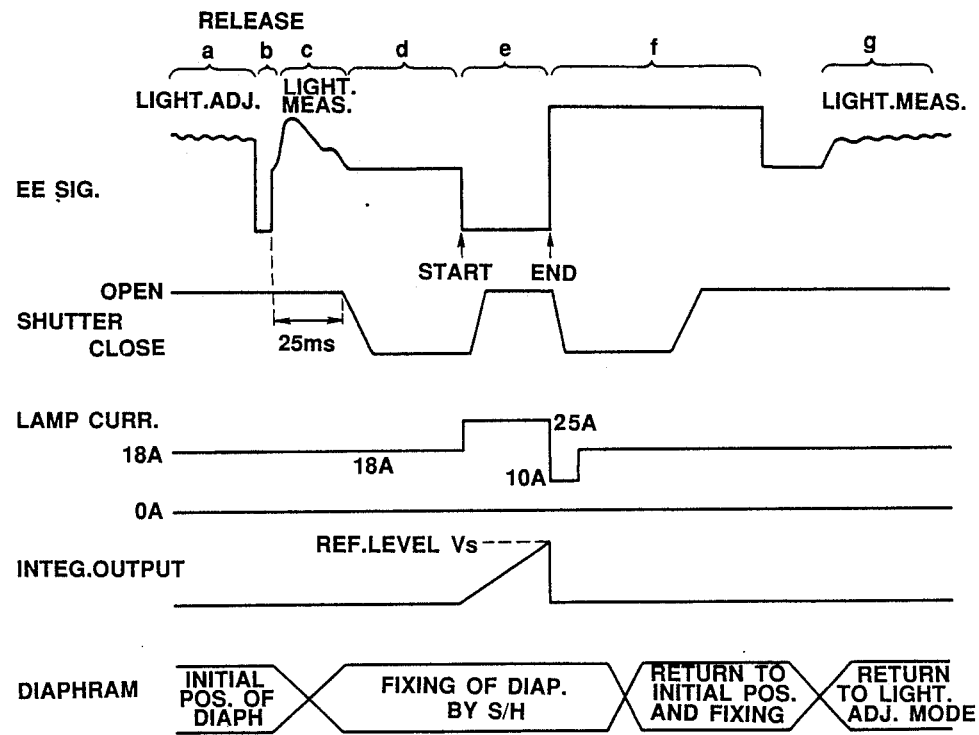
FIG. 7 shows timing charts showing the operation of the third embodiment of the present invention.

FIG. 7 shows timing charts in the third embodiment of the present invention.

In the first and second embodiments, when the release signal is input, the lamp current will be increased. However, as this invention is characterized by the diaphragming operation, after the release signal, that is, during the period of sample-holding the diaphragmed value, the lamp current need not always be increased. Therefore, in this embodiment, the lamp current is increased to 25 [A] only during the integrating period (period of e). The other operations are the same as in the first embodiment.

In this embodiment, the lamp can be made longer in the life and the apparatus can be made smaller.

By the way, in the above mentioned respective embodiments, the means of varying the illuminating light amount emitted to the object side is formed of the diaphragm 17 but a means of varying the illuminating light amount by varying the lamp current may be formed.

In the above mentioned embodiment, the diaphragm is set in the optimum position and then the shutter 18 is once closed and is again opened to actually photograph. However, without closing the shutter, the mirror 33 may be rotated to expose the film 25 and start the integrating operation.

By the way, the recording medium may be not only a still camera using the film 25 but also an electronic still camera using a CCD or the like.

As described above, according to the present invention, in case a still photographing operation is made, such illuminating light amount as a diaphragmed value will be set under the condition equal to that of a still photographing in advance and then the actual still photographing will be able to be made. Therefore, the optimum illuminating light amount can be positively set and the photographing can be made with less failures.

What is claimed is:

1. An endoscope still photographing apparatus comprising:
    an endoscope comprising an elongate insertable part, a light guide inserted through said insertable part, transmitting an illuminating light and emitting it from the end surface on the tip part side, an objective optical system arranged in the tip part of said insertable part and forming an object image and an image guide transmitting the optical image formed by said objective optical system to the end surface on the eyepiece part side;
    an endoscope still camera comprising an image forming lens fittable to said eyepiece part and forming the optical image transmitted by said image guide, a recording medium arranged in the focal plane of said image forming lens, a light receiving device receiving a part of the light amount passed through said image forming lens, a light measuring means outputting a light measuring signal corresponding to the light amount reaching said recording medium side from the signal photoelectrically converted by said light receiving device, an integrating means integrating said light measuring signal, a judging means judging whether the output level of said integrating means has reached the first reference level corresponding to the optimum exposure amount of said recording medium, a release signal generating means outputting a release indicating signal exposing said recording medium and a timer means triggered by said release indicating signal and operating said integrating means after a fixed time;
    a lamp feeding the illuminating light to the other end surface of said light guide, a diaphragm formed of an illuminating light amount varying member which can vary the passed light amount of the light of said lamp, a diaphragm diving means driving said diaphragm, a diaphragm position signal generating means outputting a signal of the level corresponding to the position of said diaphragm driven by said diaphragm driving means, a shutter intercepting the illuminating light fed to said light guide, a diaphragmed amount controlling means started by said release indicating signal and controlling to drive said diaphragm so that the level of said light measuring signal transmitted by a signal cable within said endoscope may coincide with the second reference level corresponding to the optimum illumination intensity, a holding means holding said diaphragm position signal by said diaphragmed amount controlling means and an exposure amount controlling means holding the diaphragm position signal by said holding means, then exposing said recording medium with the output of said timer means and controlling to close said shutter at the timing when the signal level on which said light measuring signal is integrated by said integrating means has reached said first reference level.

2. An endoscope still photographing apparatus according to claim 1 wherein said diaphragmed amount controlling means further controls to increase the emitted light amount of said lamp by said release signal.

3. An endoscope still photographing apparatus according to claim 1 or 2 wherein said recording medium is a film.

4. An endoscope still photographing apparatus according to any one of claims 1, or 2 wherein said endoscope still camera has a signal superimposing means superimposing the respective signals of said light measuring means, release signal generating means and judging means and outputting them to said signal cable.

5. An endoscope still photographing apparatus according to any one of claims 1 or 2 wherein said exposure amount controlling means once closes said shutter with the output of said timer means and again opens it.

6. An endoscope still photographing method in an endoscope still photographing apparatus having an optical endoscope provided with a light guide transmitting an illuminating light into an elongate insertable part and an image guide transmitting an optical image to the eyepiece part side, a still camera fittable to said eyepiece part and containing a recording medium and a light source apparatus provided with a lamp feeding an illuminating light to one end surface of said light guide, a diaphragm varying the light amount of the lamp and a shutter intercepting said light amount, whereby, without exposing said recording medium, the diaphragmed value of said diaphragm is set so that the level of the light measuring signal of the light measuring means within said still camera may coincide with the optimum exposure intensity for said recording medium, then said diaphragm is held at said diaphragmed value, said recording medium is exposed and said shutter is closed when the exposure amount to said raecording medium has reached a fixed level.

7. An endoscope still photographing method according to claim 6 wherein said recording medium is a film.

* * * * *